United States Patent [19]

Kotani

[11] Patent Number: 5,272,342
[45] Date of Patent: Dec. 21, 1993

[54] DIFFUSED LAYER DEPTH MEASUREMENT APPARATUS

[75] Inventor: Shigeo Kotani, Fujisawa, Japan
[73] Assignee: Kabushiki Kaisha Toshiba, Kawasaki, Japan
[21] Appl. No.: 912,336
[22] Filed: Jul. 13, 1992

[30] Foreign Application Priority Data

Jul. 12, 1991 [JP] Japan .................. 3-172787

[51] Int. Cl.$^5$ ...................... G01N 21/49; G01N 21/59
[52] U.S. Cl. .................... 250/341; 356/432
[58] Field of Search ................ 250/341; 356/432

[56] References Cited

U.S. PATENT DOCUMENTS 5,125,740  6/1992  Sato et al. ................ 356/128

FOREIGN PATENT DOCUMENTS 60-146132  8/1985  Japan ................. 356/432

OTHER PUBLICATIONS

M. Gál, K. Németh and G. Eppeldauer, "Method and spectrometer for measuring optical absorption in thin epitaxial layers." *Journal of Physics E*, vol. 9, No. 6, (Jun. 1976) pp. 484-487.

V. T. Prokopenko and A. D. Yas'kov, "An infrared introscope with a CO$_2$ laser for the investigation of microinhomogeneities of the structure of semiconductors." Translated from *Pribory i Tekhnika Eksperimenta*, No. 3 (May-Jun. 1974) pp. 215-216.

Primary Examiner—Constantine Hannaher
Attorney, Agent, or Firm—Foley & Lardner

[57] ABSTRACT

There is disclosed a diffused layer depth measurement apparatus equipment which has a sample table for supporting a sample cut from a measured semiconductor substrate including a high concentration impurity diffused layer on one surface side and a surface-polished low concentration diffused layer on the opposite surface side in such a manner that the one surface side of the sample is mounted on the sample table, an infrared ray generator, an infrared ray scanner for allowing infrared rays generated by the infrared ray generator to be incident from the side surface of the sample in parallel to the sample surface and for scanning the infrared ray irradiation position in a thickness direction of the sample, a transmitted light measurement unit for measuring the intensity of infrared rays transmitted through the sample, and a diffused layer depth calculation unit for calculating a ratio of a transmitted light intensity measured by the transmitted light measurement means to an incident light intensity to calculate a diffusion depth of the high concentration impurity diffused layer from the relationship between a change point of said ratio and the scanning position. A scattered light measurement unit may be used to calculate a diffusion depth of the high concentration impurity diffused layer from a change point of a scattered light intensity.

2 Claims, 5 Drawing Sheets

DIFFUSED LAYER DEPTH MEASUREMENT APPARATUS

BACKGROUND OF THE INVENTION

1. Field of the Invention

This invention relates to an apparatus for measuring a diffused layer depth of a semiconductor substrate, and more particularly to an apparatus suitable for measuring a diffusion depth of a diffused wafer used for manufacturing a discrete semiconductor such as a high output transistor or diode, etc.

2. Description of the Prior Art

In manufacturing of so called power devices such as high output transistors, diodes, or rectifying elements, etc., there is used a diffused wafer in which impurities are diffused at a high concentration at the back surface of a silicon wafer. The high concentration diffused layer of such a diffused wafer serves to reduce the series resistance at the time of forming a collector electrode of a transistor formed by using this wafer, or to reduce the ohmic contact resistance of the electrode metal.

Such a diffused wafer is conventionally manufactured as follows. First, an n⁻ type silicon substrate including phosphorus (P) doped at a low concentration, and having a resistivity of 100 Ωcm and a thickness of 1000 μm is prepared (FIG. 4A). Then, phosphorus (P) is diffused at a high concentration into such n-type silicon substrate from the surface thereof by using POCl₃ as a doping gas in the atmosphere of a temperature of about 1200° C. so that the diffusion depth $x_j$ becomes about 100 μm, thus to form n⁺ layers 21 at the both surfaces of the silicon substrate (FIG. 4B).

Since the low concentration diffused layer 20 serves as the area where regions performing device function such as emitter, base or collector, etc. of a transistor are to be formed, one side of the silicon substrate is ground so that the thickness $I_{so}$ of the low concentration diffused layer 20 is equal to 20 to 150 μm to agree with design requirements of the element, e.g., withstand voltage or current amplification factor, etc. As a result, the total thickness of the thickness $x_j$ of the high concentration diffused layer 21 and the thickness $I_{so}$ of the low concentration diffused layer 20 is equal to a thickness of several hundreds μm having a strength to an extent such that no crack occurs in handling of the wafer.

By making use of the diffused wafer obtained in this way to repeatedly implement, e.g., surface oxidation process, PEP process for forming a window for diffusion, impurity diffusion process are conducted with respect to the base and the collector to form necessary electrodes, wirings(interconnections), or a protective film or films, etc. Thus, a semiconductor device including a bipolar transistor is fabricated.

FIGS. 5A and 5B are graphs showing an impurity concentration profile in a thickness direction of the wafer. In FIG. 5A corresponding to the state of FIG. 4B, depth is taken in an x-axis direction. When such a curve is determined, it is possible to precisely obtain thicknesses of $x_j$ and $I_{so}$.

As one method for determining such an impurity concentration profile, there is known a method in which a p-type wafer of an opposite conductivity type is used to carry out diffusion, then the wafer surface is polished by the cylinder lapping method or the ball lapping method to take a cylindrical or spherical form so that the p-n diffusion surface is exposed to apply staining to allow the p-n junction to be visualized to measure the thickness of the n⁺ layer by using vernier scale.

FIG. 6 shows the state where the wafer surface is polished so as to take a form of sphere having a radius R. From the visualized position of the p-n junction, a and b are determined or calculated. By making use of these values, the thickness $x_j$ can be determined or calculated by the following formula:

$$x_j = R\{(1-b^2/R^2)^{\frac{1}{2}} - (1-a^2/R^2)^{\frac{1}{2}}\}$$

Furthermore, in order to examine the accuracy of an actual finish of the diffused wafer, the following method is used. A test piece 40 cut from a sample wafer sampled from a modulus lot is secured by means of wax on a jig having a base 31 inclined at an angle as shown in FIG. 7. Then the sample piece is obliquely polished by using a solution including abrasive or polishing agent soluted therein on a flat glass plate. The distribution of resistance values is determined while scanning the inclined surface by using two probes 43 from the n⁻ region 41 to the n⁺ region 42 as shown in FIG. 8. Then, an intersecting point of the line L1 indicating the n⁻ region and the extrapolation tangential L2 is determined as shown in FIG. 9. From this position, the Iso thickness of the n⁻ is determined.

A desired non-diffused layer thickness $I_{so}$ of the diffused wafer is precisely obtained by determining, as a polishing or abrasive clearance, the thickness obtained by subtracting total thickness of the diffusion depth $x_j$ and the non-diffused layer thickness $I_{so}$ obtained by the above-described method from the thickness of a wafer which does not undergo diffusion processing to implement polishing or abrasion thereto.

However, it is difficult to determine a precise diffused depth by using the above-described measurement method.

For example, in the polishing of the inclined surface, extremely high skillfulness is required in the work for securing a sample wafer onto a jig by wax or uniform polishing, etc. Furthermore, also in the measurement by two probes, if the n⁻ region has a resistance of more than 50 Ωcm caused a small scratch on the polished surface or absorption of abrasive, the resistivity curve in the n⁻ region does not become flat. For this reason, it is difficult to precisely determine the boundary point between the n⁻ region and the n⁺ region, giving rise to an error in determination of the n⁻ region thickness.

Furthermore, in the measurement by two probes, as shown in FIG. 10, a measured value is converted to an impurity concentration to use it as a value on the ordinate to draw a tangential at a specific concentration point, thus making it possible to determine the thickness of the n⁻ region. In this case, however, the criterion of a specific concentration (two terminal resistivity) varies depending upon the wafer maker or user. Therefore, correct measurement is not carried out. Particularly, in the case where the $I_{so}$ thickness is about 10 m, an error of as large as 50% occurs depending upon the way the tangential is drawn.

In addition, since it is required in the conventional method to prepare a special sample for measurement, an extremely troublesome work is required, resulting in the problem that it takes a long time, e.g., about 2 hours to complete the measurement.

SUMMARY OF THE INVENTION

Accordingly, an object of this invention is to provide an apparatus for measuring a diffused layer depth, which is capable of simply and precisely determining a diffused layer in a diffused wafer.

According to the present invention, there is provided an apparatus for measuring a diffused layer depth comprising:

a sample table for supporting a sample cut from a measured silicon substrate including a high concentration impurity diffused layer on one surface side and a surface polished low concentration impurity diffused layer on the opposite surface side in such a manner that the one surface side of said sample is mounted on said sample table, an infrared ray generator, infrared ray scanning means for allowing infrared rays generated by said infrared ray generator to be incident from the side surface of said sample in parallel to the sample surface, and for scanning the irradiation position of said infrared rays in a thickness direction of said sample, transmitted light measurement means for measuring the intensity of infrared rays transmitted through said sample, and diffused layer depth calculation means adapted for calculating a ratio of a transmitted light intensity measured by the transmitted light measurement means to a known incident light intensity to calculate a diffusion depth of said high concentration impurity diffused layer from the relationship between a change point of said ratio and said scanning position.

In another aspect of the invention, scattered light measurement means can be provided instead of the transmitted light measurement means, and further both measurement means can be provided.

The diffused layer depth measurement apparatus according to the present invention is based on utilization of the fact that when infrared rays are irradiated from the side surface of a sample to scan the infrared ray irradiation position in a thickness direction of the sample, the transmission factor or scattering factor suddenly changes at the boundary portion between a region having high impurity concentration and a region having a low impurity concentration. Namely, such a sudden change is detected to determine the scanning position at that time. Thus, the depth of the diffused layer can be determined precisely and simply.

DESCRIPTION OF THE PREFERRED EMBODIMENT

A preferred embodiment will now be described with reference to the attached drawings.

The principle employed in this invention will be first described.

Figure 2:
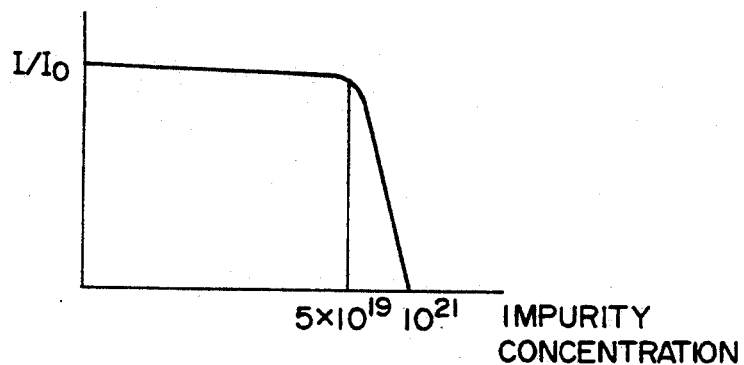
FIG. 2 is a graph showing the relationship between the impurity concentration and the infrared ray transmission factor.
Figure 3:
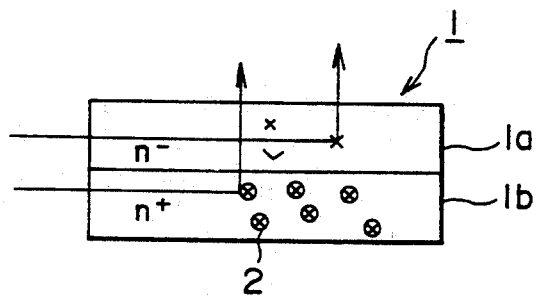
FIG. 3 is an explanatory view showing the reason why the infrared transmission factor is lowered in the high concentration region.
Figure 4A:
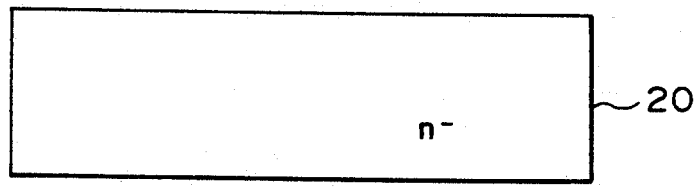
FIGS. 4A-4C are cross sectional views every process steps showing a manufacturing of a diffused wafer.
Figure 4B:
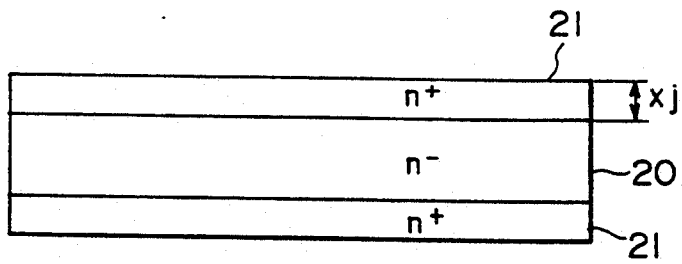
Figure 4C:
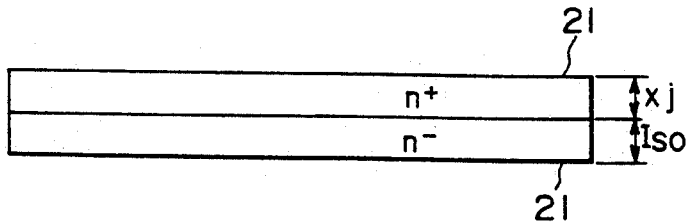
Figure 5A:
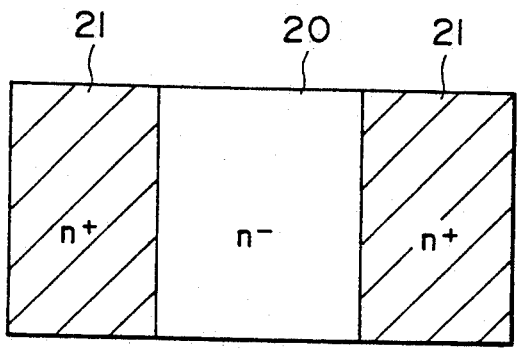
FIGS. 5A and 5B are graphs showing the impurity concentration distribution under the state where diffusing process is implemented to a wafer.
Figure 5B:
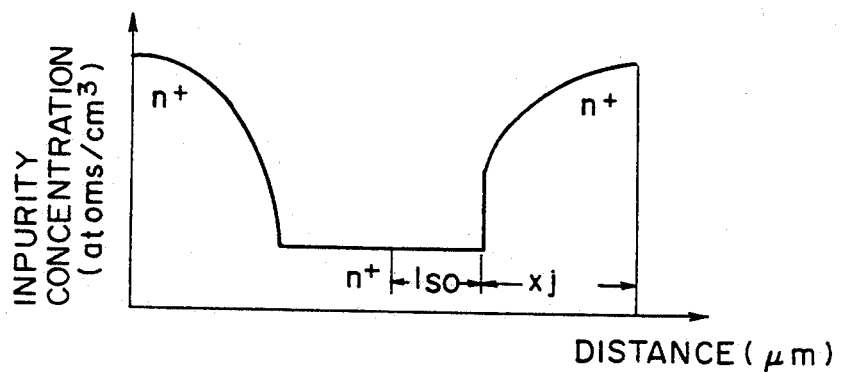
Figure 6:
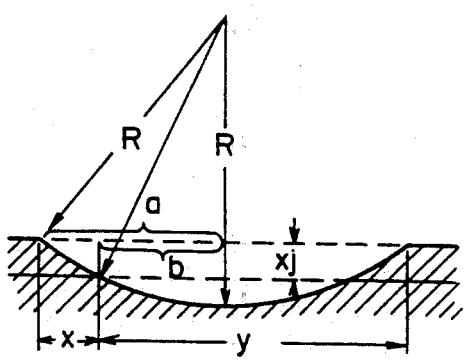
FIG. 6 is an explanatory view showing the principle of the diffusion depth measurement by ball lapping conventionally carried out.
Figure 7:
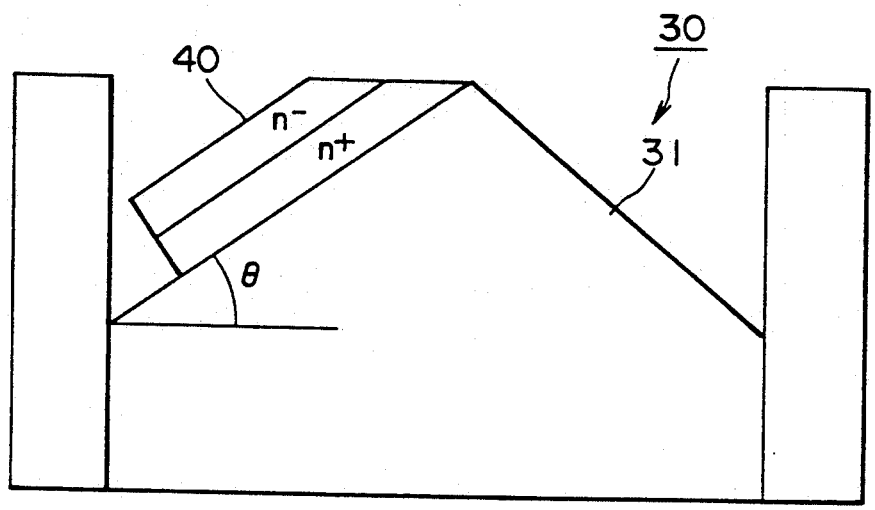
FIG. 7 is an explanatory view for explaining a conventional processing of a sample required for measurement by the conventional two-probe method.
Figure 8:
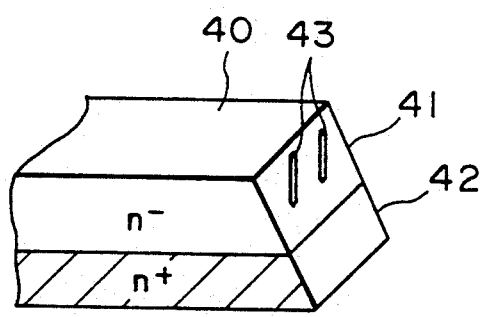
FIG. 8 is an explanatory view of the conventional two-probe method.
Figure 9:
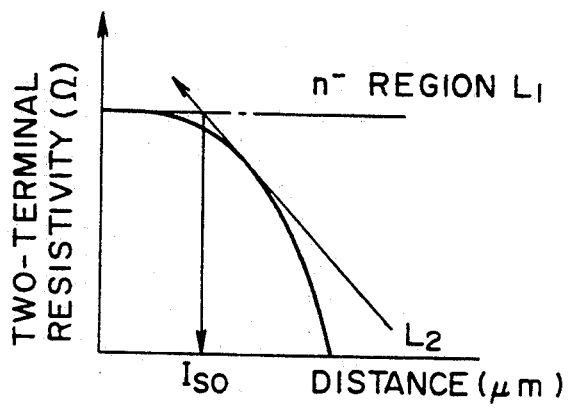
FIG. 9 is an explanatory view showing a manner of determining position of the n- region from a change of the resistivity in the conventional two-probe method.
Figure 10:
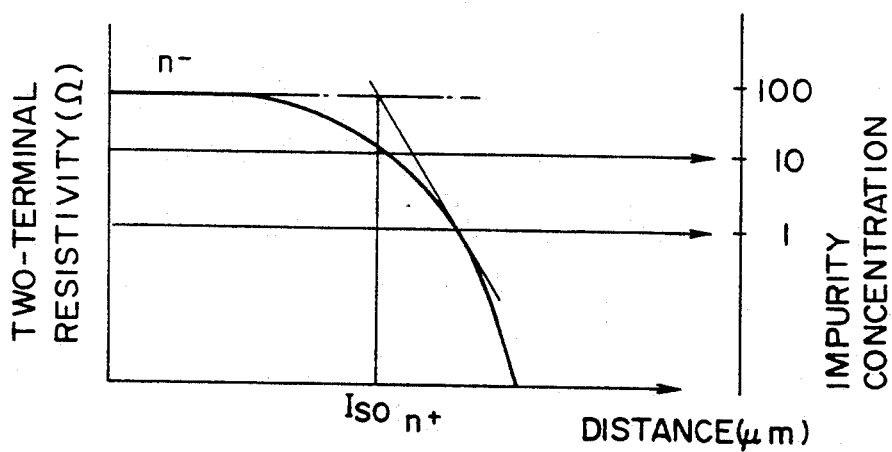
FIG. 10 is an explanatory view showing a manner of converting resistivity to impurity concentration to determine a position of the n- region in the conventional two-probe method.

In this invention, there is utilized the phenomenon that the transmission factor of infrared ray in silicon crystal suddenly attenuates, as shown in FIG. 2, when the impurity concentration is higher than $5 \times 10^{19}/cm^3$. This phenomenon takes place as described below. Namely, since the impurity is diffused at a temperature as high as 1250° to 1300° C., there is, in the N⁻ region, precipitation defects due to oxygen existing in crystal. Furthermore, since high concentration diffusion close to the solid-solution limit is carried out in the N+ region, an extraordinary precipitation of impurity, or crystal defects 2 called pipes occur as shown in FIG. 3. As a result, these defects serve as scattering nuclei with respect to the incident infrared rays, giving rise to a phenomenon as mentioned above. Accordingly, in the N+ region 1b of the silicon substrate 1, scattering takes place to a more degree as compared to that in the N⁻ region 1a. As a result, the transmission factor suddenly lowers. Accordingly, if the scanning position where the transmission factor or the scattering factor suddenly changes is determined, the diffused layer depth can be determined.

Figure 1:
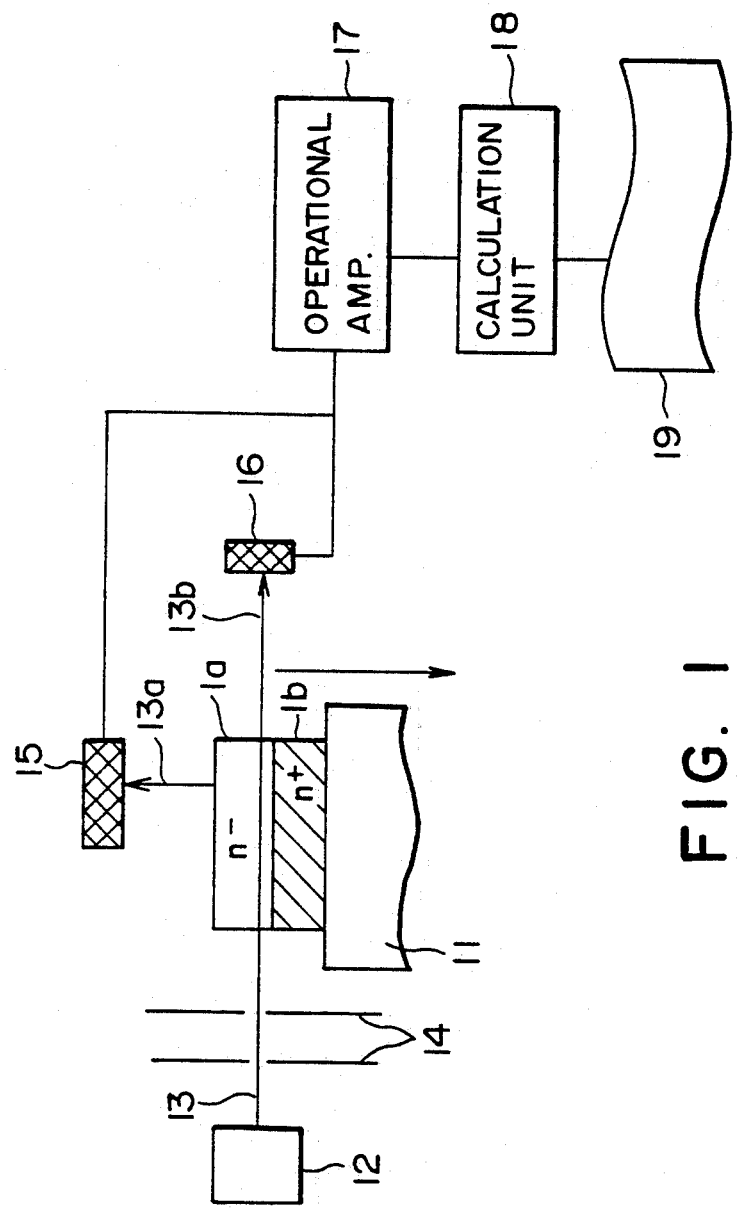
FIG. 1 is a block diagram showing the outline of the system configuration of a diffused layer depth measurement apparatus according to this invention.

FIG. 1 is a block diagram showing the outline of the configuration of an embodiment of a diffused layer depth measurement apparatus according to this invention.

This apparatus comprises a sample table 11 adapted to support thereon a sample respectively provided at higher and lower parts with a low concentration impurity diffused layer 1a and a high concentration impurity diffused layer 1b, and driven upwardly and downwardly by a drive mechanism (not shown); an infrared ray generator 12 for generating infrared rays 13 from the lateral direction of the sample table 11; slits 14 for converging infrared rays 13 generated at the infrared ray generator 12 to conduct them to the sample; a first detector 15 provided above the sample table 11 and adapted to detect a scattered light 13a scattered in the sample, and a second detector 16 provided on the optical axis of infrared rays generated at the infrared ray generator 12 and adapted to detect a transmitted light 13b transmitted through the sample. Furthermore, as the signal processing system, there are provided an operational amplifier 17 for amplifying outputs of the first and second detectors, a calculation unit 18 for implementing a predetermined operation to an output of the operational amplifier 17 to determine a diffused layer depth, and a printer 19 for printing out the calculated result.

As a sample used in this apparatus, a piece obtained by simply cutting a portion of a silicon substrate is used. In this instance, the dimensional accuracy of the length thereof is not particularly required. For example, it is sufficient that the length is about 2 to 6 mm. It is, however, desirable that the sample end surface is polished by etching in order to prevent any unnecessary scattering on the cross section.

As a light source of the infrared ray generator 12, a light source having high coherency and easy beam scanning is desirably used. It is preferable that, e.g., YAG laser light source is used. Furthermore, it is desirable that the detection characteristics of the first and second detectors are in correspondence with each other from a viewpoint of improvement in the measurement accuracy.

The measurement using such a diffused layer depth measurement apparatus is carried out as follows.

Infrared rays 13 are generated from the infrared ray generator 12 to irradiate infrared rays onto a sample through slits 14. A scattered light thereof is detected by the first detector 15, and a transmitted light thereof is detected by the second detector 16. Outputs of these detectors are amplified at the operational amplifier 17. At the calculation unit 18, a ratio with respect to an infrared ray intensity known in advance is determined. Thus, a scattering factor and a transmission factor are determined. The sample table 11 is adapted so that it can scan in upper and lower directions of FIG. 1 as previously described. Thus, it is possible to continuously observe changes of the scattering factor and the transmission factor.

In a substrate including a diffused layer, in shifting from the n$^-$ region to the n$^+$ region, the transmission factor of the infrared ray suddenly decreases, or the scattering factor suddenly increases. Accordingly, by determining the position where such a change takes place, it is possible to determine the depth at which the impurity diffused layer arrives.

By detecting the point where the transmission factor suddenly changes, it is possible to very easily and precisely determine an impurity diffused layer depth. Similarly, a method of detecting the point where the scattering factor suddenly changes may be used for this purpose.

While, in the above-described embodiment, scanning is carried out from the low concentration region to the high concentration region, a scanning in a direction opposite to the above may be carried out. Moreover, scanning in this case is only required that the relationship between the irradiation position of the infrared ray and the position in a thickness direction of a sample changes relative to each other. Accordingly, there may be employed, in place of moving the sample table as in the embodiment, an arrangement such that the infrared ray generator side moves in upper and lower directions.

Furthermore, while, in the above-described embodiment, the transmission factor indicating a ratio of a transmitted light intensity to the known infrared ray intensity or the scattering factor indicating a ratio of scattered light intensity to the known infrared ray intensity are used, a ratio between an output of the first detector and an output of the second detector may be used. In this case, since both an output suddenly increasing and an output suddenly decreasing are used, a more sudden change can be provided.

In addition, an approach may be employed to prepare in advance, as data base, the relationship between the impurity concentration and the transmission factor or the scattering factor with respect to samples having a unit length to compare it with a measured value, thus to more precisely determine the concentration distribution.

In accordance with this invention, an approach is employed to determine the diffusion depth in the high concentration region by scanning in a depth direction of the sample by making use of the phenomenon that when the impurity concentration in silicon is above a fixed value, the transmission factor or the scattering factor of the infrared ray suddenly changes. Thus, it is possible to simply carry out a precise diffusion depth measurement without providing preparation of a special sample or a special measurement.

What is claimed is:

1. An apparatus for measuring a diffused layer depth comprising:
    a sample table for supporting a sample cut from a measured silicon substrate including a high concentration impurity diffused layer on one surface side and a surface polished low concentration impurity diffused layer on the opposite surface side in such a manner that the one surface side of said sample is mounted on said sample table,
    an infrared ray generator,
    infrared ray scanning means for allowing infrared rays generated by said infrared ray generator to be incident from the side surface of said sample in parallel to the sample surface, and for scanning the irradiation position of said infrared rays in a thickness direction of said sample,
    scattered light measurement means provided above said sample and adapted to measure the intensity of infrared rays scattered in said sample, and
    diffused layer depth calculation means adapted for calculating a ratio of a scattered light intensity measured by the scattered light measurement means to a known incident light intensity to calculate a diffusion depth of said high concentration impurity diffused layer from the relationship between a change point of said ratio and said scanning position.

2. An apparatus for measuring a diffused layer depth comprising:
    a sample table for supporting a sample cut from a measured silicon substrate including a high concentration impurity diffused layer on one surface side and a surface polished low concentration impurity diffused layer on the opposite surface side in such a manner that the one surface side of said sample is mounted on said sample table,
    an infrared ray generator,
    infrared ray scanning means for allowing infrared rays generated by said infrared ray generator to be incident from the side surface of said sample in parallel to the sample surface, and for scanning the irradiation position of said infrared rays in a thickness direction of said sample,
    transmitted light measurement means for measuring the intensity of infrared rays transmitted through said sample, scattered light measurement means provided above said sample and adapted to measure the intensity of infrared rays scattered in said sample, and diffused layer depth calculation means adapted for calculating a ratio of a transmitted light intensity measured by said transmitted light measurement means to a scattered light intensity measured by said scattered light measurement means to calculate a diffusion depth of said high concentration impurity diffused layer from the relationship between a change point of said ratio and said scanning position.

* * * * *